United States Statutory Invention Registration [19]

[11] Reg. Number: H184

Koppes et al. [43] Published: Jan. 6, 1987

[54] 2,2,2-TRIFLUOROETHOXY BIS(2-FLUORO-2,2-DINITROETHOXY)METHANE AND A METHOD PREPARATION

[75] Inventors: William M. Koppes, Adelphi; Horst G. Adolph, Silver Spring, both of Md.

[73] Assignee: The United States of America as represented by the Secretary of the Navy, Washington, D.C.

[21] Appl. No.: 878,150

[22] Filed: Jun. 23, 1986

[51] Int. Cl.[4] ..... C07C 43/00; C07C 79/34

[52] U.S. Cl. ..... 568/590; 149/19.3; 149/88

*Primary Examiner*—John F. Terapane
*Assistant Examiner*—Susan Wolffe
*Attorney, Agent, or Firm*—Kenneth E. Walden; Roger D. Johnson

[57] ABSTRACT

2,2,2-trifluoroethoxy bis(2-fluoro-2,2-dinitroethoxy)methane, $CF_3CH_2OCH[OCH_2CF(NO_2)_2]_2$, is an energetic plasticizer useful in plastic-bonded explosives. Of particular importance is its miscibility with fluoropolymers.

3 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

2,2,2-TRIFLUOROETHOXY BIS(2-FLUORO-2,2-DINITROETHOXY)METHANE AND A METHOD PREPARATION

BACKGROUND OF THE INVENTION

This invention relates to plastic-bonded explosives and more particularly to energetic plasticizers for plastic-bonded explosives.

Examples of energetic plasticizers which are currently used in plastic-bonded explosives (PBXs) are bis(2-fluoro-2,2-dinitroethyl)formal (FEFO), butanetriol trinitrate (BTTN), and trimethylolethane trinitrate (TMETN). These compounds have various disadvantages which include limited thermal stability (BTTN, TMETN), high volatility (FEFO), toxicity (FEFO), and high melting point (FEFO). In addition, these energetic plasticizers are not miscible with fluoropolymers and can therefore not be used with these desirable new binder materials for PBXs.

SUMMARY OF THE INVENTION

Accordingly, an object of this invention is to provide a novel organic compound.

Another object of this invention is to provide a new energetic plasticizer for plastic-bonded explosives.

A further object of this invention is to provide an energetic plasticizer having good thermal stability.

Still another object of this invention is to provide an energetic plasticizer having a low volatility.

Yet a further object of this invention is to provide an energetic plasticizer that is miscible with fluoropolymers.

These and other objects of this invention are achieved by providing a new compound 2,2,2-trifluoroethoxy bis(2-fluoro-2,2-dinitroethoxy)methane and a method of preparing it.

DETAILED DESCRIPTION OF THE PREFERRED EMBODIMENT

This invention provides 2,2,2-trifluoroethoxy bis(2-fluoro-2,2-dinitroethoxy)methane (TFF) which has been found to act as a plasticizer for various energetic and non-energetic prepolymers commonly used in plastic-bonded explosive (PBX) formulations. TFF is a liquid with a melting point of −3° to −1° C. and a density of 1.63g/cm$^3$ (at 25° C.). Its heat of formation is estimated to be −400.0 kcal/mol and the calculated detonation pressure is 232 kbar.

The advantages of TFF as an energetic plasticizer are illustrated by comparing its properties with those of bis(2-fluoro-2,2-dinitroethyl)formal (FEFO), the plasticizer it is intended to replace. The melting point of FEFO is 14° C., that of TFF is −3° to −1° C. Thus, TFF is significantly lower melting, a highly desirable feature which will convey better low-temperature properties to plastic-bonded explosives (PBXs) using TFF instead of FEFO. The volatility of TFF and FEFO were compared by thermogravimetric analysis (TGA) at 117° C. The observed weight-losses were 0.028 mg/min and 0.039 mg/min, respectively. Thus, TFF is less volatile than FEFO. This will facilitate processing and increase the storage life of TFF containing PBXs. One of the most serious drawbacks of FEFO is its propensity to induce allergic skin reactions in many people coming in contact with it. To date, TFF has not shown this undesirable handling side-effect. The most significant difference between TFF and FEFO is, however, the miscibility of TFF with certain fluorinated prepolymers (e.g., Fluorel, Viton A). This permits the formulation of energetic binders based on the use of chemically and thermally stable fluoropolymers.

2,2,2-trifluoroethoxy bis(2-fluoro-2,2-dinitroethoxy)methane, $CF_3CH_2OCH[OCH_2CF(NO_2)_2]_2$, can be prepared from 2-fluoro-2,2-dinitroethanol, $CF(NO_2)_2CH_2OH$, by the following reaction sequence as illustrated in Examples 1, 2, and 3:

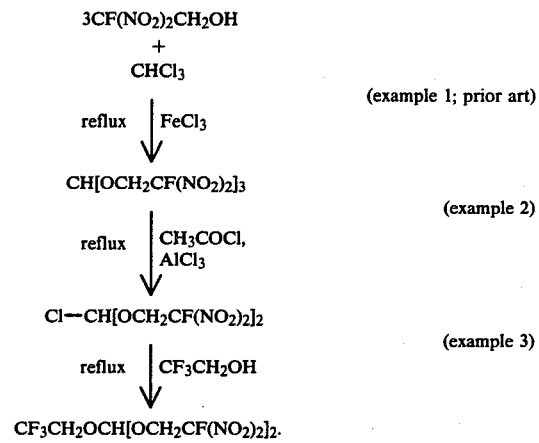

Tris(2-fluoro-2,2-dinitroethoxy)methane, $CH[OCH_2CF(NO_2)_2]_3$, is a prior art compound which is synthesized by reacting three moles of 2-fluoro-2,2-dinitroethanol with one mole of chloroform by refluxing the reactants in the presence of ferric chloride as a catalyst. The conditions of this reaction are illustrated by example 1 which is incorporated from U.S. Pat. No. 3,388,147, entitled "2-Fluoro-2,2-Dinitroethyl Carbonates and Production thereof," which was issued on June 11, 1968, to Mortimer J. Kamlet et al. (see col. 3, example III).

Next, the tris(2-fluoro-2,2-dinitroethoxy)methane is refluxed with aluminum chloride and acetyl chloride to produce chloro bis(2-fluoro-2,2-dinitroethoxy)methane as illustrated by example 2.

Finally, one mole of 2,2,2-trifluorethanol is reacted with each mole of chloro bis(2-fluoro-2,2-dinitroethoxy)methane to produce the desired product 2,2,2-trifluoroethoxy bis(2-fluoro-2,2-dinitroethoxy)methane under conditions illustrated by example 3. The choice of a solvent for this step is not critical. Any inert solvent in which the reactants are soluble and which has a suitable boiling point may be used. Suitable solvents include dichloromethane, 1,1-dichloroethane, 1,2-dichloroethane, 1,1,2-trichloroethane, or mixtures thereof.

The general nature of the invention having been set forth, the following examples are presented as specific examples thereof. It will be understood that the invention is not limited to these specific examples but is susceptible to various modifications that will be recognized by one of ordinary skill in the art.

EXAMPLE 1

(Prior Art)

Tris(2-fluoro-2,2-dinitroethoxy)methane

[i.e., tris(2-fluoro-2,2-dinitroethyl)orthoformate]

"A mixture of 0.5 g. anhydrous ferric chloride and 10 ml. chloroform was placed in a 30 ml. round-bottom flask fitted with a magnetic stirrer and a reflux condenser connected through a bubbler to a methanol gas trap. 2-fluoro-2,2-dinitroethanol, 2.0 g. (0.013 mole) was added and the mixture stirred and refluxed for 24 hours, after which time the mixture was collected [sic] to room temperature and the solvent removed in vacuo.

The residue was drowned in iced water, stirred until the ferric chloride dissolved and the crystalline product collected. Recrystallization of this material from chloroform-hexane gave 1.39 g. (68%) pure tris(2-fluoro-2,2-dinitroethyl)orthoformate (FDNEOF) as fine colorless needles, M.P. 110°–11.2°."

EXAMPLE 2

Chloro bis(2-fluoro-2,2-dinitroethoxy)methane

A solution of tris(2-fluoro-2,2-dinitroethoxy)methane (23.6 g, 0.050 mol), aluminum chloride (12.0 g, 0.090 mol) and acetyl chloride (200 g) was refluxed for 1.5 hours and then concentrated on a rotary evaporator to a viscous liquid. This was extracted with chloroform (2×50 ml). After treatment with activated charcoal (2 g), this solution was filtered and concentrated (rot. evap., 40° C. bath) to 23 g of residue from which 8.53 g (87%) of 2-fluoro-2,2-dinitroethyl acetate (bp 40°–3° C./0.1 mm) was removed by distillation. The residual liquid (14.14 g, 80% yield) was chloro bis(2-fluoro-2,2-dinitroethoxy)methane, free of contaminants by $^1H$ NMR analysis. Anal. Calcd for $C_5H_5ClF_2N_4O_{10}$: C, 16.94; H, 1.42; Cl, 10.00; F, 10.72; N, 15.80. Found: C, 17.10; H, 1.78; Cl, 10.08; F, 10.71; N, 15.42.

EXAMPLE 3

2,2,2-Trifluoroethoxy bis(2-fluoro-2,2-dinitroethoxy)methane

Chloro bis(2-fluoro-2,2-dinitroethoxy)methane (14.11 g, 0.0348 mol), prepared in example 2, was refluxed with 5.00 g (0.0500 mol) of 2,2,2-trifluoroethanol in 30 ml of dichloroethane for 2.5 hours. The solution was filtered through 5 g of Silica Gel 60 (EM Reagents) in a short column, followed by a rinse with 50 ml of dichloromethane. Concentration of the solution on a rotary evaporator gave 17 g of liquid residue which was distilled to give a forerun of 2.60 g (bp 37°–48° C./0.04 mm). This was a mixture of 2-fluoro-2,2-dinitroethanol and 2-fluoro-2,2-dinitroethoxy bis(2,2,2-trifluoroethoxy)methane. It was followed by a 1.60 g fraction of pure 2-fluoro-2,2-dinitroethoxy bis(2,2,2-trifluoroethoxy)methane (bp 49° C./0.05mm). The pot residue of 10.98 g. (66%) was the desired product 2,2,2-trifluoroethoxy bis(2-fluoro-2,2-dinitroethoxy)methane with a trace of tris(2-fluoro-2,2-dinitroethoxy)methane by TLC and NMR analysis: bp 99°–103° C./0.025 mm; $^1H$ NMR ($CDCl_3$): δ5.67 (s, 1), 4.80 (d, 4, J=17 Hz), 4.03 (q, 2, J=8 Hz).

Anal Calcd for $C_7H_7F_5N_4O_{11}$: C, 20.10; H, 1.69; F, 22.72; N, 13.40. Found: C, 20.37; H, 1.42; F, 22.46; N, 13.16.

To those skilled in the art, many modifications and variations of the present invention are possible in light of the above teachings. It is therefore to be understood that the present invention can be practiced otherwise than as specifically described herein and still be within the spirit and scope of the appended claims.

What is claimed as new and desirable to be secured by Letters Patent of the United States is:

1. 2,2,2-trifluoroethoxy bis(2-fluoro-2,2-dinitroethoxy)methane, $CF_3CH_2OCH[OCH_2CF(NO_2)_2]_2$.

2. A method of preparing 2,2,2-trifluoroethoxy bis(2-fluoro-2,2-dinitroethoxy)methane comprising the following steps in order:

(1) refluxing tris(2-fluoro-2,2-dinitroethoxy)methane with aluminum chloride and acetyl chloride to produce chloro bis(2-fluoro-2,2-dinitroethoxy)methane;

(2) reacting one mole of 2,2,2-trifluoroethanol with each mole of the chloro bis(2-fluoro-2,2-dinitroethoxy)methane to produce 2,2,2-trifluoroethoxy bis(2-fluoro-2,2-dinitroethoxy)methane; and (3) isolating the product 2,2,2-trifluoroethoxy bis(2-fluoro-2,2-dinitroethoxy)methane.

3. The process of claim 2 wherein the reaction in step (2) is run under reflux in a solvent selected from the group consisting of dichloromethane, 1,1-dichloroethane, 1,2-dichloroethane, 1,1,2-trichloroethane, and mixtures thereof.

* * * * *